(12) United States Patent
Hardahl et al.

(10) Patent No.: US 7,991,458 B2
(45) Date of Patent: *Aug. 2, 2011

(54) SYSTEM AND A METHOD FOR ANALYSING ECG CURVATURE FOR LONG QT SYNDROME AND DRUG INFLUENCE

(75) Inventors: Thomas Bork Hardahl, Aalborg (DK); Claus Graff, Klarup (DK); Mads Peter Andersen, Aalborg (DK); Egon Toft, Aalborg (DK); Johannes Jan Struijk, Aalborg (DK); Joergen Kim Kanters, Aalsgaarde (DK)

(73) Assignee: Aalborg Universitet, Aalborg OE (DK)

( * ) Notice: Subject to any disclaimer, the term of this patent is extended or adjusted under 35 U.S.C. 154(b) by 1108 days.

This patent is subject to a terminal disclaimer.

(21) Appl. No.: 10/596,617

(22) PCT Filed: Oct. 20, 2004

(86) PCT No.: PCT/DK2004/000722
§ 371 (c)(1),
(2), (4) Date: Feb. 5, 2007

(87) PCT Pub. No.: WO2005/058156
PCT Pub. Date: Jun. 30, 2005

(65) Prior Publication Data
US 2007/0208264 A1    Sep. 6, 2007

(30) Foreign Application Priority Data
Dec. 19, 2003 (EP) .................................. 03029363

(51) Int. Cl.
*A61B 5/0472* (2006.01)
(52) U.S. Cl. ......... 600/516; 600/509; 600/515; 600/517

(58) Field of Classification Search .................. 600/508, 600/509, 515–517
See application file for complete search history.

(56) References Cited

U.S. PATENT DOCUMENTS

| 5,419,338 A | 5/1995 | Sarma et al. |
| 5,749,367 A | 5/1998 | Gamlyn et al. |
| 5,803,084 A | 9/1998 | Olson |
| 6,324,423 B1 | 11/2001 | Callahan et al. |
| 6,389,308 B1 | 5/2002 | Shusterman |
| 6,684,100 B1 * | 1/2004 | Sweeney et al. ............. 600/517 |
| 6,925,324 B2 | 8/2005 | Shusterman |
| 2002/0143263 A1 * | 10/2002 | Shusterman .................. 600/509 |

FOREIGN PATENT DOCUMENTS

| GB | 2 387 442 A | 10/2003 |
| JP | 11-512012 A | 10/1999 |
| WO | WO 91/19452 | 12/1991 |
| WO | 97/08989 A1 | 3/1997 |

* cited by examiner

*Primary Examiner* — Scott M Getzow
*Assistant Examiner* — Joseph M Dietrich
(74) *Attorney, Agent, or Firm* — Roberts Mlotkowski Safran & Cole, P.C.; David S. Safran

(57) ABSTRACT

The present invention relates to a system or method for analyzing drug influence on ECG curvature and Long QT Syndrome. The system has an input means connected to an ECG source, where different parameters of a received ECG curvature are indicated and/or isolated for indicating possible symptoms which relate to certain diseases that influence the ECG curvature. The aim of the invention is to achieve a system and a method for diagnosing Long QT Syndrome in an objective, fast and effect way by indication of a number of symptoms derivable from an ECG curve. Further aim is to achieve an effective test of drug influence on ECG curvature. The system analyzes the QT curvature of the ECG curvature for indicating Long QT Syndrome.

17 Claims, 14 Drawing Sheets

SYSTEM AND A METHOD FOR ANALYSING ECG CURVATURE FOR LONG QT SYNDROME AND DRUG INFLUENCE

The present invention relates to a system for analysing drug influence on ECG curvature and Long QT Syndrome where at least one among a number of different parameters is isolated, which system has an input means connected to an ECG source, where the different parameters of a received ECG curvature are indicated and/or isolated and for indicating possible symptoms.

The present invention further relates to a method for analysing drug influence on ECG curvature, which curvature contains a number of parameters.

The heart generates an electrical signal which can be measured as an ECG, which can be recorded as an ECG diagram. The waves in the ECG-signal P, Q, R, S, T and U are due to depolarisation and repolarisation of the heart.

Figure 1:
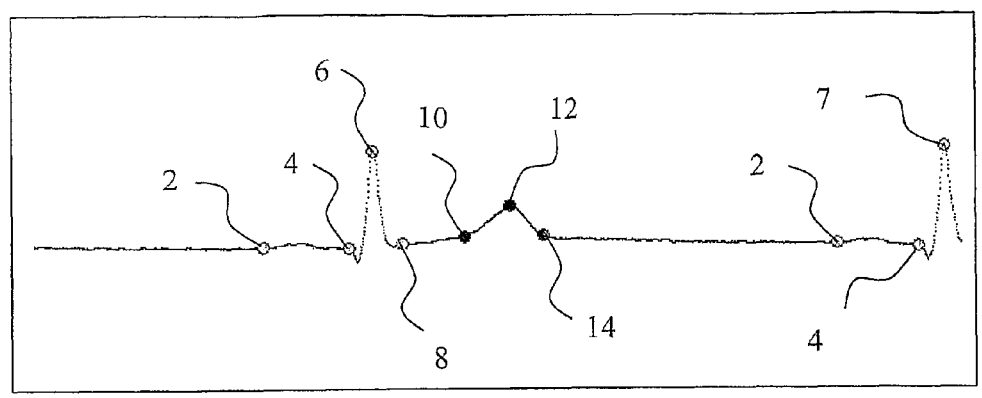

Intervals and complexes are illustrated on a typical ECG curvature, see FIG. 1 in order to illustrate the different curve sections isolated by the analysis and referred to by parameters, intervals and complexes comprising the following annotations, where Ponset 2 marks the beginning of the P wave.
Qonset 4 marks the beginning of the Q wave.
Rpeak 6 marks the top of the R wave.
The Jpoint 8 marks the end of the S wave.
Tstart 10 marks the beginning of the T wave.
Tpeak marks 12 the top of the T wave.
Tend 14 marks the end of the T wave.
The QT interval starts at Qonset 4 and ends at Tend 14.
The QT curvature is the part of the ECG curvature between Qonset 4 and Tend 14.
The RR interval goes from one R-peak 6 to the following R-peak 7.

U.S. Pat. No. 5,749,367 describes a heart monitoring apparatus and method wherein an electrocardiograph signal is obtained from a patient and processed to enhance the salient features and to suppress noise. A plurality n of values representative of the features of the electrocardiograph signal are generated and used in a Kohonen neural network to generate an n dimensional vector. This vector is compared with a stored plurality m of n dimensional reference vectors defining an n dimensional Kohonen feature map to determine the proximity of the vector to the reference vectors. If it is determined by the Kohonen neural network that the vector is within or beyond a threshold range of the reference vectors, a signal is the output, which can be used to initiate an event such as the generation of an alarm or the storage of ECG data.

US 2002/143263 describes a system comprised of a medical device and a method for analyzing physiological and health data and representing the most significant parameters at different levels of detail, which are understandable to a lay person and a medical professional. Low, intermediate and high-resolution scales can exchange information between each other for improving the analyses; the scales can be defined according to the corresponding software and hardware resources. A low-resolution Scale I represents a small number of primary elements such as the intervals between the heart beats, duration of electrocardiographic PQ, QRS, and QT-intervals, amplitudes of P-, Q-, R-, S-, and T-waves. This real-time analysis is implemented in a portable device that requires minimum computational resources. The set of primary elements and their search criteria can be adjusted using intermediate or high-resolution levels. At the intermediate-resolution Scale II, serial changes in each of the said elements can be determined using a mathematical decomposition into series of basis functions and their coefficients. This scale can be implemented using a specialized processor or a computer organizer. At the high-resolution Scale III, combined serial changes in all primary elements can be determined to provide complete information about the dynamics of the signal. This scale can be implemented using a powerful processor, a network of computers or the Internet. The system can be used for personal or group self-evaluation, emergency or routine ECG analysis or continuous event, stress-test or bed-side monitoring.

The aim of the invention is to achieve a system and a method for diagnosing Long QT Syndrome in an objective, fast and effective way by indication of a number of symptoms derivable from an ECG curve. A further aim of the invention is to achieve an effective test of drug influence on ECG curvature.

This can be achieved with the system previously described if a first number of selected parameters from at least three main groups, which groups comprise parameters of symmetry, flatness, duration and/or complexity, which parameters are combined in at least a first mathematical analysis, which relate to or are indications of certain diseases, where said diseases are known to influence the ECG curvature, where the result of the analysis can be represented as a point in a coordinate system comprising at least one axis where the system can compare the actual placement in the coordinate system with a number of reference parameters stored in the system for indicating symptoms or diseases having influence on the ECG curvature, where the system analyses the QT curvature of the ECG curvature for indicating Long QT syndrome.

Hereby, it is achieved that any symptom of Long QT Syndrome having an indication (influence) in the ECG curvature can be detected in an objective, automated and very fast way. The system might be used under field conditions such as in ambulances or in other situations where a fast indication of heart diseases is needed in order to help the patient in a correct way as early as possible. The analysis that takes place in an ambulance on its way to the hospital can by transmitting the results to the hospital allow the doctor at the hospital to give feedback to the personnel in the ambulance so that the correct treatment of the patient may start. At the same time, the hospital can prepare the correct activity for the incoming patient. The system could be very important for ECG analyses for all non-specialists in the field if they have to analyse an ECG curvature.

The system can analyse drug influence on a number of persons, where analyses are made before and repeated after drug influence, where selected parameters are compared and/or combined. It is, hereby, achieved that a drug might be tested for having influence on the ECG curvature of a number of persons. This can be very important for acceptance of new drugs. This system and also described as a method is able to relatively short period, and where the decision if a new drug should be rejected because of having negative influence of the ECG, or the drug can be accepted. This decision can be taken relatively fast.

The scope of the invention can also be fulfilled with a method for analysing the drug influence on the ECG curvature if the method incorporates the steps of:
receiving ECG curvature from a source,
indicating a number of different parameters contained in the received ECG curvature,
storing the parameters in storage means,
selecting disease specific parameters in the storage means
selecting parameters from at least three groups, which groups comprise parameters of symmetry, flatness, duration and/or complexity combining selected parameters in mathematical analysing means representing the result of the mathematical analysis as a point in a coordinate system comprising at least one axis, comparing the actual placement in the coordinate system with a number of reference parameters stored in a memory, analysing the QT curvature of the ECG for indicating drug induced changes.

In this way as already described, a very effective analysis of the ECG curvature is achieved.

The analysing process can be repeated in the system for further selected parameters in order to achieve more reliable results. Hereby, it is achieved that the system or the method can be repeated several times with different combinations of parameters. With the system, a deviation of parameters from the stored data indicating symptoms of Long QT Syndrome or drug influence may also be interpreted for farther reference.

The system or method analyses the parameters chosen from at least three main groups, such as groups of parameters of symmetry, flatness, complexity and duration relating to the actual ECG curvature. In this way, it is achieved that the parameters are grouped cific number of possible parameters. Keeping the number of parameters relatively small, the analysis takes place in a faster way.

The group of symmetry might comprise at least the following parameters:

S1 Symmetry evaluated from Tstart to Tend, calculated by the formula:

$$S1 = \left( \sum_{n=Tstart}^{Tend} (n - m_1)^3 \cdot w[n] \right)^{\frac{1}{3}},$$

where $w[n] = v[n]/m_0,$ $$m_1 = \sum_{n=Tstart}^{Tend} n \cdot w[n],$$

$$m_0 = \sum_{n=Tstart}^{Tend} v[n]$$

and v[n] is the ECG signal.

S2 Symmetry with Tpeak as mean evaluated from Tstart to Tend, calculated by the formula:

$$S2 = \left( \sum_{n=Tstart}^{Tend} (n - Tpeak)^3 \cdot w[n] \right)^{\frac{1}{3}},$$

where $w[n] = v[n]/m_0,$ $$m_0 = \sum_{n=Tstart}^{Tend} v[n]$$

and v[n] is the ECG signal.

S3 Symmetry with Tpeak as mean evaluated in a symmetric interval of 10% of the Tstart-Tend-interval surrounding Tpeak, calculated by the formula:

$$S3 = \left( \sum_{n=Tpeak-0.05 \cdot (Tend-Tstart)}^{Tpeak+0.05 \cdot (Tend-Tstart)} (n - Tpeak)^3 \cdot w[n] \right)^{\frac{1}{3}},$$

where $w[n] = v[n]/m_0,$ $$m_0 = \sum_{n=Tstart}^{Tend} v[n]$$

and v[n] is the ECG signal.

S4 Symmetry with Tpeak as mean evaluated in a symmetric interval of 20% of the Tstart-Tend-interval surrounding Tpeak, calculated by the formula:

$$S4 = \left( \sum_{n=Tpeak-0.1 \cdot (Tend-Tstart)}^{Tpeak+0.1 \cdot (Tend-Tstart)} (n - Tpeak)^3 \cdot w[n] \right)^{\frac{1}{3}},$$

where $w[n] = v[n]/m_0,$ $$m_0 = \sum_{n=Tstart}^{Tend} v[n]$$

and v[n] is the ECG signal.

S5 Ratio of the time interval "Tstart to Tpeak" and the time interval "Tpeak to Tend", calculated by the formula:

$$S5 = \frac{Tpeak - Tstart}{Tend - Tpeak}$$

S6 Ratio of the average slope from Tstart to Tpeak and from Tpeak to Tend $$S6 = \frac{Slope_{Tstart,Tpeak}}{Slope_{Tpeak,Tend}},$$

where $$Slope_{Tstart,Tpeak} = \frac{v[Tpeak] - v[Tstart]}{Tpeak - Tstart}$$

$$Slope_{Tstart,Tend} = \frac{v[Tend] - v[Tpeak]}{Tend - Tpeak}$$

and v[n] is the ECG signal.

S7 Variation evaluated from Tstart to Tend, calculated by the formula:

$$S7 = \left( \sum_{n=Tstart}^{Tend} (n - m_1)^2 \cdot w[n] \right)^{\frac{1}{2}},$$

where $w[n] = v[n]/m_0,$ $$m_1 = \sum_{n=Tstart}^{Tend} n \cdot w[n],$$

-continued $$m_0 \sum_{n=Tstart}^{Tend} v[n]$$

and v[n] is the ECG signal.

S8 Variation with Tpeak as mean evaluated from Tstart to Tend, calculated by the formula:

$$S8 = \left( \sum_{n=Tstart}^{Tend} (n - Tpeak)^2 \cdot w[n] \right)^{\frac{1}{2}},$$

where $$w[n] = v[n]/m_0,$$

$$m_0 = \sum_{n=Tstart}^{Tend} v[n]$$

and v[n] is the ECG signal.

S9 Variation with Tpeak as mean evaluated in a symmetric interval of 10% of the Tstart-Tend-interval surrounding Tpeak, calculated by the formula:

$$S9 = \left( \sum_{n=Tpeak-0.05 \cdot (Tend-Tstart)}^{Tpeak+0.05 \cdot (Tend-Tstart)} (n - Tpeak)^2 \cdot w[n] \right)^{\frac{1}{2}},$$

where $$w[n] = v[n]/m_0,$$

$$m_0 = \sum_{n=Tstart}^{Tend} v[n]$$

and v[n] is the ECG signal.

S10 Variation with Tpeak as mean evaluated in a symmetric interval of 20% of the Tstart-Tend-interval surrounding Tpeak, calculated by the formula:

$$S10 = \left( \sum_{n=Tpeak-0.1 \cdot (Tend-Tstart)}^{Tpeak+0.1 \cdot (Tend-Tstart)} (n - Tpeak)^2 \cdot w[n] \right)^{\frac{1}{2}}.$$

where $$w[n] = v[n]/m_0,$$

$$m_0 = \sum_{n=Tstart}^{Tend} v[n]$$

and v[n] is the ECG signal.

S11 The Hill parameter, $K_m$, evaluated by least square fitting of the repolarisation integral, RI(t), from the Jpoint to the following Ponset as described by Kanters et al., "T wave morphology analysis distinguishes between KvLQT1 and HERG mutations in long QT syndrome", Heart Rhythm (2004) 3, 285-292:

$$RI(t) = V_{max} \left( \frac{t^n}{K_m^n + t^n} \right)$$

S12 The Hill parameter, $K_m$, evaluated by least square fitting of the repolarisation integral, RI(t), from Tstart to Tend analogous to the method described by Kanters et al., "T wave morphology analysis distinguishes between KvLQT1 and HERG mutations in long QT syndrome", Heart Rhythm (2004) 3, 285-292:

$$RI(t) = V_{max} \left( \frac{t^n}{K_m^n + t^n} \right)$$

F1 Flatness evaluated from Tstart to Tend, calculated by the formula:

$$F1 = \left( \sum_{n=Tstart}^{Tend} (n - m)^4 \cdot w[n] \right)^{\frac{1}{4}},$$

where $$w[n] = v[n]/m_0,$$

$$m_1 = \sum_{n=Tstart}^{Tend} n \cdot w[n],$$

$$m_0 = \sum_{n=Tstart}^{Tend} v[n]$$

and v[n] is the ECG signal.

F2 Flatness parameter, F1, normalized by the size of the R wave, calculated by the formula:

$$F2 = \frac{F1}{|v[Rpeak] - v[Jpoint]|},$$

where v[n] is the ECG signal.

F3 Flatness with Tpeak as mean evaluated from Tstart to Tend, calculated by the formula:

$$F3 = \left( \sum_{n=Tstart}^{Tend} (n - Tpeak)^4 \cdot w[n] \right)^{\frac{1}{4}},$$

where $$w[n] = v[n]/m_0,$$

$$m_0 = \sum_{n=Tstart}^{Tend} v[n]$$

and v[n] is the ECG signal.

F4 Flatness parameter, F3, normalized by the size of the R wave, calculated by the formula:

$$F4 = \frac{F3}{|v[Rpeak] - v[Jpoint]|},$$

where v[n] is the ECG signal.

F5 Flatness with Tpeak as mean evaluated in a symmetric interval of 10% of the Tstart-Tend-interval surrounding Tpeak, calculated by the formula:

$$F5 = \left( \sum_{n=Tpeak-0.05\cdot(Tend-Tstart)}^{Tpeak+0.05\cdot(Tend-Tstart)} (n-Tpeak)^4 \cdot w[n] \right)^{\frac{1}{4}},$$

where $$w[n] = v[n]/m_0,$$

$$m_0 = \sum_{n=Tstart}^{Tend} v[n]$$

and v[n] is the ECG signal.

F6 Flatness parameter, F5, normalized by the size of the R wave, calculated by the formula:

$$F6 = \frac{F5}{|v[Rpeak] - v[Jpoint]|},$$

where v[n] is the ECG signal.

F7 Flatness with Tpeak as mean evaluated in a symmetric interval of 20% of the Tstart-Tend-interval surrounding Tpeak, calculated by the formula:

$$F7 = \left( \sum_{n=Tpeak-0.1\cdot(Tend-Tstart)}^{Tpeak+0.1\cdot(Tend-Tstart)} (n-Tpeak)^4 \cdot w[n] \right)^{\frac{1}{4}},$$

where $$w[n] = v[n]/m_0,$$

$$m_0 = \sum_{n=Tstart}^{Tend} v[n]$$

and v[n] is the ECG signal.

F8 Flatness parameter, F7, normalized by the size of the R wave, calculated by the formula:

$$F8 = \frac{F7}{|v[Rpeak] - v[Jpoint]|},$$

where v[n] is the ECG signal.

F9 Ratio of the total area under the T-wave from Tstart to Tpeak and the corresponding time interval, calculated by the formula:

$$F9 = \frac{\sum_{n=Tstart}^{Tpeak} v[n]}{Tpeak - Tstart},$$

where v[n] is the ECG signal.

F10 Flatness parameter, F9, normalized by the size of the R wave, calculated by the formula:

$$F10 = \frac{F9}{|v[Rpeak] - v[Jpoint]|},$$

where v[n] is the ECG signal.

F11 Ratio of the total area under the T-wave from Tpeak to Tend and the corresponding time interval, calculated by the formula:

$$F11 = \frac{\sum_{n=Tpeak}^{Tend} v[n]}{Tend - Tpeak},$$

where v[n] is the ECG signal.

F12 Flatness parameter, F11, normalized by the size of the R wave, calculated by the formula:

$$F12 = \frac{F11}{|v[Rpeak] - v[Jpoint]|},$$

where v[n] is the ECG signal.

F13 Ratio of the total area under the T-wave from Tstart to Tend and the corresponding time interval, calculated by the formula:

$$F13 = \frac{\sum_{n=Tstart}^{Tend} v[n]}{Tend - Tstart},$$

where v[n] is the ECG signal.

F14 Flatness parameter, F13, normalized by the size of the R wave, calculated by the formula:

$$F14 = \frac{F13}{|v[Rpeak] - v[Jpoint]|},$$

where v[n] is the ECG signal.

F15 Ratio of the T wave height and the T wave width, calculated by the formula:

$$F15 = \frac{v[Tpeak]}{Tend - Tstart},$$

where v[n] is the ECG signal.

F16 The T wave height, calculated by the formula:

$$F16 = v[Tpeak],$$

where v[n] is the ECG signal.

F17 Average slope from Tstart to Tpeak, calculated by the formula:

$$F17 = \frac{v[Tpeak] - v[Tstart]}{Tpeak - Tstart},$$

F18 Average slope from Tpeak to Tend, calculated by the formula:

$$F18 = \frac{v[Tend] - v[Tpeak]}{Tend - Tpeak},$$

where v[n] is the ECG signal.

F19 The Hill parameter, n, evaluated by least square fitting of the repolarisation integral, RI(t), from the Jpoint to the following Ponset as described by Kanters et al., "T wave morphology analysis distinguishes between KvLQT1 and HERG mutations in long QT syndrome", Heart Rhythm (2004) 3, 285-292:

$$RI(t) = V_{max}\left(\frac{t^n}{K_m^n + t^n}\right)$$

F20 The Hill parameter, n, evaluated by least square fitting of the repolarisation integral, RI(t), from Tstart to Tend analogous to the method described by Kanters et al., "T wave morphology analysis distinguishes between KvLQT1 and HERG mutations in long QT syndrome", Heart Rhythm (2004) 3, 285-292:

$$RI(t) = V_{max}\left(\frac{t^n}{K_m^n + t^n}\right)$$

F21 The Hill parameter, $V_{max}$, evaluated by least square fitting of the repolarisation integral, RI(t), from the Jpoint to the following Ponset as described by Kanters et al., "T wave morphology analysis distinguishes between KvLQT1 and HERG mutations in long QT syndrome", Heart Rhythm (2004) 3, 285-292:

$$RI(t) = V_{max}\left(\frac{t^n}{K_m^n + t^n}\right)$$

F22 The Hill parameter, $V_{max}$, evaluated by least square fitting of the repolarisation integral, RI(t), from Tstart to Tend analogous to the method described by Kanters et al., "T wave morphology analysis distinguishes between KvLQT1 and HERG mutations in long QT syndrome", Heart Rhythm (2004) 3, 285-292:

$$RI(t) = V_{max}\left(\frac{t^n}{K_m^n + t^n}\right)$$

QTc The Q-T interval normalized by the square root of the R-R interval according to Bazett's formula:

$$QTc = \frac{Tend - Qonset}{\sqrt{RR}}$$

D2 The time interval from Tstart to Tend, calculated by the formula:

$$D2 = Tend - Tstart$$

D3 The time interval from Tstart to Tpeak, calculated by the formula:

$$D3 = Tpeak - Tstart$$

D4 The time interval from Tpeak to Tend, calculated by the formula:

$$D4 = Tend - Tpeak$$

The group of complexity might contain at least the following parameters:

C1: Number of local maxima between Tstart and Tend; the minimum number is one.

C2: Number of phases between Tstart and Tend, where a phase is defined as a singly connected part of the wave that is entirely above or entirely below the iso-electric line; the minimum number is one.

The parameters previously described can also be calculated and stored as intra- and inter-lead means and standard deviations.

The groups of parameters could contain further parameters, and the groups may contain a number of subgroups.

When combining parameters from different groups, a much better result is achieved than when only using parameters from the same group. The parameters can be an elevation of the curve; they can be the morphology of the curve; or they could be time-deviations as an example of possible parameters. When combining parameters, a precise analysis can take place because a specific combination of parameters can indicate Long QT Syndrome or drug influence on ECG curvature and it is possible to effectively select between ECG-signals that look very much alike, but which indicate dif-A selection of these parameters is possible so that special genetic combinations are known with reference to the different stored parameters. The system can be updated by new data selected from different sources.

The system and/or method can analyse the QT curvature of the ECG for indicating Long QT syndrome. This way, the Long QT syndrome can be indicated in an objective and effective manner which might occur in postsyncopal cardiac examination.

The method can differentiate between different genotypes of the Long QT Syndrome, which is important for the treatment. It can, hereby, be achieved that the correct medical treatments can be started. The system and the method can be used for test of drug influence on ECG curvature.

The system can be trained, where the parameters' values are calculated for individual subjects, where an analysis of the parameters is performed such as a pattern classification method based on supervised learning, such as Discriminant Analysis, Nearest Neighbor Techniques, Multilayer Neural Networks, Decision Trees and Rule Based Methods or combinations of these.

The final classification function is at least based on data from at least one LQT or drug influenced group and Normal subjects stored as a training set with the consequences that the classification method is improved by adding new subjects to the training set, which new subject can be tailored to demographic or gender differences. In addition it is achieved that reference values based on the training set can be selected from the most critical group of persons with reference to the parameters that are going to be tested.

Once the parameters' values are calculated for individual subjects the mathematical analysis chooses the optimal (small) parameter set out of the complete set (large) from all categories, which values are stored as ref values. It should be made clear that the final classification functions are based on data from at least one LQT or drug influenced group and Normal subjects (the training set) with the consequences that the discrimination method can be improved, in principle, by adding new subjects to the training set, but also that the method can be tailored to demographic differences (for example in California LQT2 patients might be somewhat different than in Denmark: the method can cope with this simply by training the system with people from California for use in California and with people from Denmark for use in Denmark) or to other differences (for example gender differences). Other examples could be age differences, difference between infants and adults.

This invention also comprises the use of a system for analysing ECG curvature for test of drugs, which system has input means connected to an ECG source, wherein at least one among a number of different parameters is isolated and stored in the system, where the different parameters of a received ECG curvature are indicated and/or isolated for indicating possible symptoms, where a number of selected parameters, are combined in at least a first mathematical analysis, where the result of the analysis is represented as a point in at least one coordinate system, comprising at least one axis, where the system compares the actual placement in the coordinate system with a number of reference parameters stored in the system, for indicating symptoms having influence on the ECG curvature, and analysing the QT curvature of the ECG for indicating drug induced changes to the ECG curvature, where the parameters of the ECG curvature are calculated before and after a drug test for a number of subjects, where the difference for selected parameters between before and after testing is calculated for each subject, where a mathematical analysis of selected parameters for a number of subjects gives statistical significance for at least one of the following decisions:
"accept of the drug",
"rejection of the drug".
"further testing of the drug".

A very effective way of accepting or rejecting a drug is achieved.

Below are described one possible method and a system to illustrate the invention.

The Long QT Syndrome is a genetic disorder characterized by abnormal cardiac repolarisation resulting in prolonged QT duration, syncopal episodes and increased risk of than 90% of all LQTS patients. The QT interval duration is the only ECG-based quantifier of LQTS used in clinical practice today. However duration is only a gross estimate of repolarisation and does not allow perfect discrimination between KvLQT1, HERG and normal subjects. Studies have shown that T-wave morphology parameters are useful discriminators in LQTS, but no single parameter has proven to be sufficient. In this study we present a novel multivariate discrimination method based on a combination of T-wave symmetry-, flatness- and duration parameters. 16 subjects were included in the study—8 normal, 5 HERG and 3 KvLQT1 patients. Genotypes were known for all LQTS patients, but one. Standard 12—lead ECG's were recorded on each subject. An automatic ECG event detection algorithm was implemented. The signal was highpass filtered and normalized with respect to the isoelectric level to ensure a stable baseline. 4 parameters describing the duration of repolarisation, 6 symmetry- and 15 flatness parameters were calculated to characterize each of the T-waves. The mean values of lead V5 and the interlead standard deviations were used as parameter values. Stepwise discriminant analysis was performed to obtain two discriminant functions based on the five strongest discriminatory parameters. The resulting discriminant functions include 2 duration-, 2 symmetry- and 1 flatness parameter. The two functions classify all subjects correctly (p>0.0001, p<0.005). Further discriminant analysis with a reduced number of parameter categories implied that superior classification is obtained when using all three parameter categories presented. A combination of parameters from the three categories symmetry, flatness and duration of repolarisation was sufficient to correctly classify ECG recordings from the KvLQT1, HERG and normal subjects in this study. This multivariate approach may prove to be a powerful clinical tool.

1. INTRODUCTION

The Long QT Syndrome (LQTS) represents a hereditary genetic disorder characterized by the presence of prolonged QT duration on the ECG, syncopal episodes due to polymorphic ventricular tachycardia (torsade de pointes), and arrythmogenic sudden cardiac death.

Mutations involving 6 different genes have been identified in LQTS subjects. These mutations result in structural and functional changes in ion-channel proteins and cur-repolarisation patterns. The most prevalent genes affected in LQTS patients are KvLQT1 and HERG which account for more than 90% of LQTS genotype patients. The current study focuses on carriers of these two genes. Although some attempts have been made to develop quantitative measures that link different repolarisation abnormalities to specific LQTS related channel-opathities these methods have so far failed to provide a solid diagnostic yield. In current practice the duration of the QT interval is the only widely accepted quantifier of ventricular repolarisation. Yet, it has been recognized that the duration of the QT interval is only a gross estimate of repolarisation since T-wave morphology is also important when characterizing the QT interval. This is evidenced by the fact that approximately 10% of all mutation carriers have a normal Bazett corrected QTc (<440 ms) and 40% of KvLQT1 and HERG carriers show QTc values between 410-470 ms that overlap with non-carriers. Conversely only 2% of all carriers present with a normal ST-T pattern and a normal QT interval. Morphological aberrations thus carry major implications for the identification of abnormal repolarisation and have been included as diagnostic criteria equivalent to that of a positive family history for LQTS.

Studies have shown that affected KvLQT1 patients generally show broad based T-waves with a normal to relatively high amplitude and often without a distinct T-wave onset. For individuals with mutations involving the HERG gene the aforementioned studies have generally found low amplitude T-waves with bifid T-waves in 60% or more of the carriers.

Cardiologists already include a qualitative assessment of T-wave morphology from the ECG in order to obtain information that augments the clinically established QT interval measurement and facilitates discrimination between LQTS genotypes. However qualitative description of repolarisation morphology may be biased due to intra- and interpersonal variability thus indicating the need for a standardized quantitative measure of this parameter.

In the following is presented a novel multivariate categorization method that allows discrimination between KvLQT1, HERG and normal individuals based on Twave morphology recorded from 12-lead ECG's. Hallmark morphological features of T-ing three primary T-wave characteristics to be assessed. These characteristics are symmetry, flatness and duration.

2. METHODS 2.1 Subjects

The study included ECG recordings from 8 female and 8 male subjects. The subjects were divided into four groups; 3 KvLQT1 (aged 20-48, 2 females), 5 HERG (aged 13-76, 2 females), 8 normal (aged 23-31, 4 females). Genotypes were known for all KvLQT1 and HERG subjects with a single exception: 1 patient was categorized as a KvLQT1 subject by anamnesis and ECG-analysis. In the normal group there were no reports of prior cardiac diseases or LQTS family precedent.

2.2 Data Collection

Data acquisition was carried out with the subjects resting in supine position. The equipment used for data acquisition was a portable digital ECG recording system, "Cardio Perfect Resting ECG system" manufactured by Cardiocontrol. Recording was divided into three sessions. Data was collected from 8 leads (I-III, V2-V6) with a sampling rate of 1200 Hz. Signal recording length was 75 s. in the first session and 150 s. in the last two sessions.

Following data acquisition, SCP files generated by the Cardio perfect software were exported from a MSDE/SQL7 server and subsequently converted to .MAT files using SCP-Batch Converter.

2.3 Algorithm for Detection of Events in the ECG

To facilitate evaluation of the repolarisation process and the QT interval, several events in the ECG were detected (Qstart, Rtop, Tstart, Ttop and Tend). An algorithm for detecting these events was implemented in Matlab 6.0.

Figure 2:
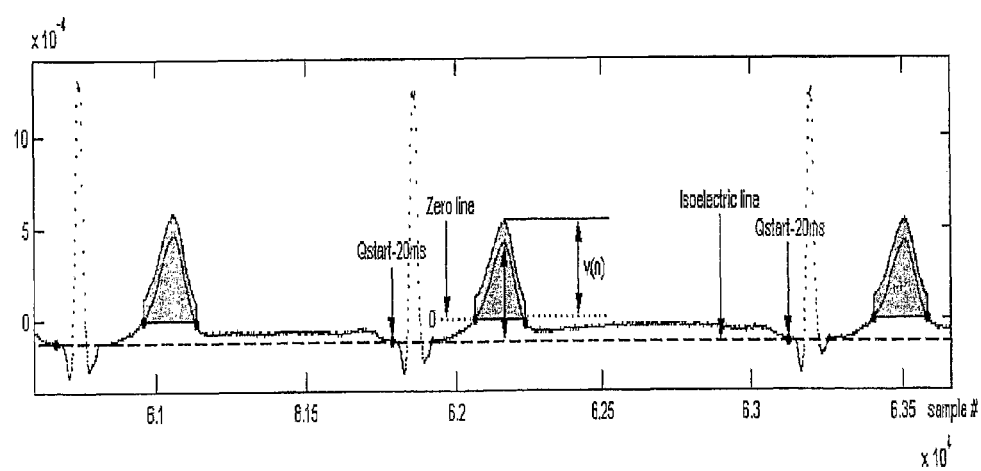

The method is based on prior work published by Laguna et al. and uses adaptive thresholding techniques applied to a digitally filtered and differentiated signal. A minor extension to the algorithm was incorporated to enable the detection of Tstart. Tstart was detected with a technique equivalent to the technique for detecting Tend. FIG. 2 shows an example of the result of the event detection algorithm.

FIG. 2. Important events that are used to describe repolarisation are marked by dots by the event detection algorithm. The algorithm is able to detect the events on all 8 recorded leads.

2.4 Preliminary Signal Processing

Evaluation of the QT interval and the repolarisation process was done on the basis of an ECG signal with stabilized baseline. This was achieved through preliminary signal processing. The "raw" ECG was filtered by a Kaiser window high pass filter with a cut-off frequency of 0.5 Hz, 40 dB damping in 0.25 Hz and 0.1 dB ripple in the pass-band. Other filters are subsequently used: a lowpassfilter for noise reduction and a notch filter for reduction of 50 Hz or 60 Hz interference. The isoelectric line is defined as the straight line that connects the PQ interval before the QT interval at hand and the PQ interval after the QT interval at hand. The iso-electric line relative to zero is subtracted from the QT interval analysed. After filtering, the signal had an almost stable baseline. In order to improve stability, isoelectric lines in the signal were estimated from one P-Q interval (Qstart minus 20 ms) to the following P-Q interval (Qstart minus 20 ms). The signal was then normalized by subtracting the line value from the corresponding signal values. This process is shown in FIG. 2.

2.5 T-Wave Morphology Parameters

In order to characterize the T-wave morphology, a number of parameters were selected. The parameters were chosen to cover each of the three categories: Twave symmetry, T-wave flatness and duration. The parameters are listed and described in table 1.

Parameters S1-S4 and F1-F8 is based on the calculation of modified skewness and kurtosis measures defined as symmetry and flatness in the following. Inspired by the summary measures of probability distributions used in the field of statistics the T-waves were modelled as probability mass distributions (FIG. 3) and assigned a centre (mean), width (standard deviation), an asymmetry measure and a convexity measure.

Asymmetry and convexity calculations were then carried out based on the modified skewness and kurtosis measures ($3^{rd}$ and $4^{th}$ order moments) as follows:

The total area under the signal, m0, was calculated:

$$m_0 = \sum_{n=0}^{N-1} V[n]$$

The signal was normalized by the value of the area, m0:

$w[n]=v[n]/m_o$

Normalization facilitated the calculation of the moment functions, since w[n] shares a fundamental property with the probability mass function: A total area of 1. The $1^{st}$ order moment, m1, was calculated. m1 is the mean of the signal:

$$m_1 = \sum_{n=0}^{N-1} n*w[n]$$

The $2^{nd}$ order moment, m2, was calculated. m2 is the standard deviation of the signal:

$$m_2 = \left(\sum_{n=0}^{N-1} (n-m_1)^2 * w[n]\right)^{1/2}$$

FIG. 2 Isoelectric lines (dashed lines) in the signal are calculated from one P-Q interval to the following P-Q interval (Qstart–20 ms). The line values are subtracted from the corresponding ECG signal values giving the distances v(n). The result of this procedure is shown as an area plot with basis on the zero-line.

Figure 3:
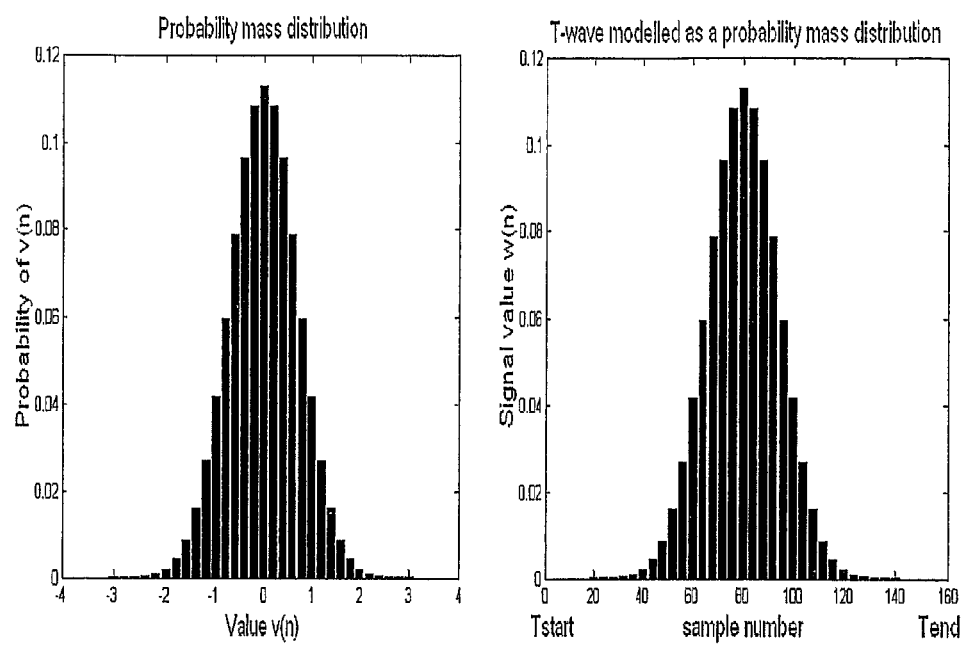

FIG. 3. a) Example probability mass distribution used when calculating standard skewness and kurtosis measures. b) Modified frequency distribution used in this study for calculating the modified skewness and kurtosis measures. Signal values v(n) are shown in FIG. 2.

Parameter Description

Symmetry

S1 Skewness evaluated from Tstart to Tend.
S2 Skewness evaluated from Tstart to Tend with Ttop as mean.
S3 Skewness evaluated in a symmetric interval, 10% of the Tstart-Tend interval surrounding Ttop with Ttop as mean.
S4 Skewness evaluated in a symmetric interval, 20% of the Tstart-Tend interval surrounding Ttop with Ttop as mean.
S5 Ratio of the time interval from Tstart to Ttop and the time interval from Ttop to Tend.
S6 Ratio of the average slope from Tstart to Ttop and from Ttop to Tend.

Flatness

F1 Kurtosis evaluated from Tstart to Tend.
F2 F1 normalized by the absolute Rtop-Qnadir value.
F3 Kurtosis evaluated from Tstart to Tend with Ttop as mean.
F4 F3 normalized by absolute Rtop-Qnadir value.
F5 Kurtosis evaluated in a symmetric interval, 10% of the Tstart-Tend interval surrounding Ttop with Ttop as mean.
F6 F5 normalized by absolute Rtop-Qnadir value.
F7 Kurtosis evaluated in a symmetric interval, 20% of the Tstart-Tend interval surrounding Ttop with Ttop as mean.
F8 Kurtosis normalized by the value of Rtop with Ttop as mean.

F9 Ratio of the total area under the T-wave from Tstart to Ttop and the corresponding time interval.
F10 F9 normalized by absolute Rtop-Qnadir value.
F11 Ratio of the total area under the T-wave from Ttop to Tend and the corresponding time interval.
F13 Ratio of the total area under the T-wave from Tstart to Tend and the corresponding time interval.
F14 F13 normalized by absolute Rtop-Qnadir value.
F15 Ratio of the height of Rtop and the width of the Tstart-Tend interval.
Duration
QTc The Q-T interval normalized by the square root of the R-R interval according to Bazett's formula.
D2 Time interval from Tstart to Tend.
D3 Time interval from Tstart to Ttop.
D4 Time interval from Ttop to Tend.

The table above shows a Complete list of the parameters used to characterize T-wave morphology. Parameters belong to one of three categories: symmetry, flatness and duration.

The $3^{rd}$ order moment, m3, was calculated. m3 is the modified skewness of the signal:

$$m_3 = \left( \sum_{n=0}^{N-1} (n-m_1)^3 * w[n] \right)^{\frac{1}{3}}$$

Finally the $4^{th}$ order moment, m4, was calculated. m4 is the modified kurtosis of the signal:

$$m_4 = \left( \sum_{n=0}^{N-1} (n-m_1)^4 * w[n] \right)^{1/4}$$

2.6 Data Analysis in Matlab

The T-wave morphology parameters for the acquired, pre-processed ECG recordings were evaluated using Matlab 6.0. Only valid data were analyzed—i.e. data from leads where the signal was not corrupted by high frequency noise and where the event detection algorithm was successful in detecting the relevant events with satisfactory precision. Parameter means and standard deviations were calculated for every T-wave in the signal on all leads. A great interlead variation in T-wave morphology may be an indicator of LQTS. Interlead variance was therefore examined by calculating the standard deviation of the lead means for each parameter.

Only the parameter means from lead V5 and interlead standard deviations were used as final parameter values. Hence, for every parameter in table 1, two parameters were calculated—one with index "meanV5" and one with index "std" e.g. F1meanV5 and F1std.

2.7 Statistical Analysis

In order to characterize and classify data from the three groups (KvLQT1, HERG and normal), the evaluated parameter values were processed using discriminant analysis. The analysis was carried out in SPSS version 11.5. The objective of the discriminant analysis was twofold: finding parameters that most efficiently discriminate between the groups and reducing the number of variables. Therefore a stepwise procedure was used with the Mahalanobis D2 as the most appropriate distance measure.

The entry/removal-criteria were adjusted in order to reduce the number of variables in the discriminant functions to achieve a 1:3 ratio between the number of variables and the population size (N=16). The criteria were empirically chosen to be pentry=0.045 and premoval=0.09 providing the desired 5 variables in the discriminant functions.

Figure 4:
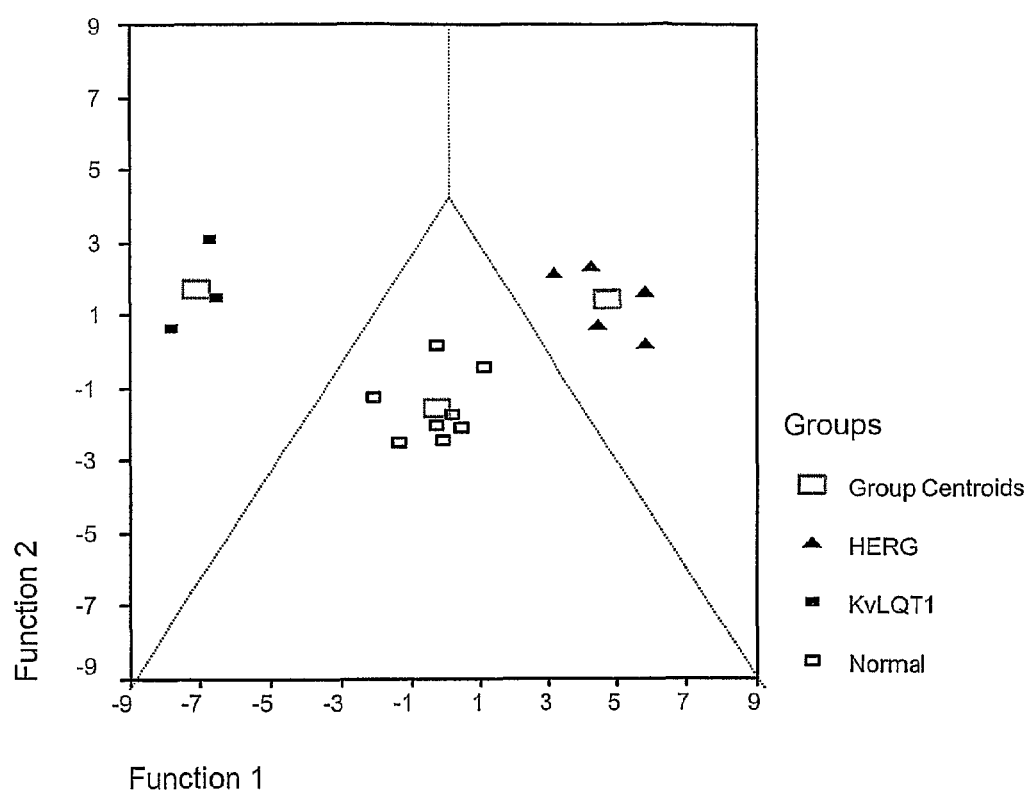
Figure 5A:
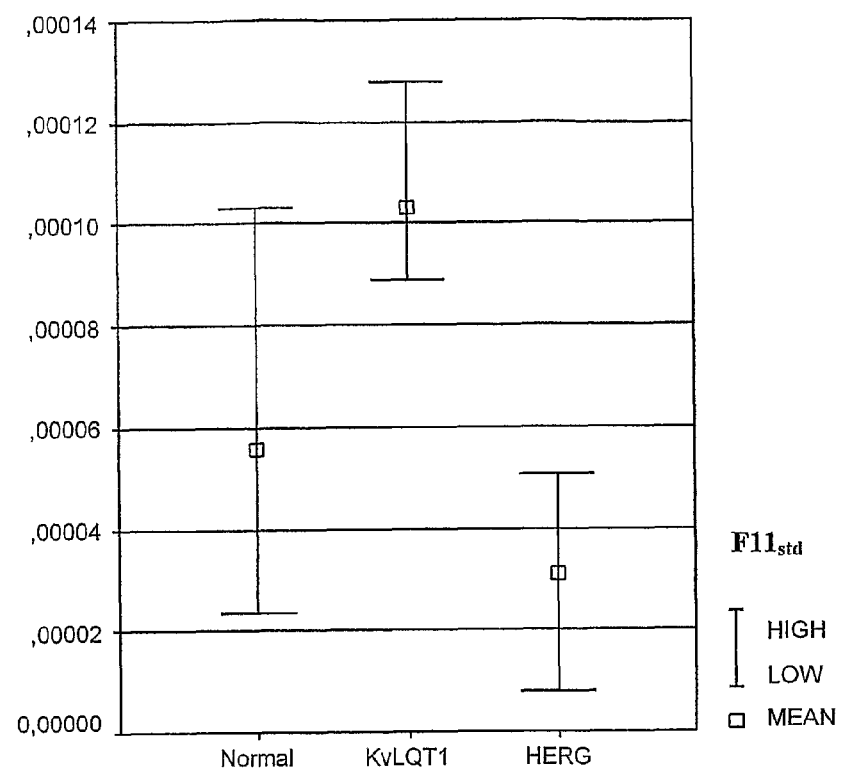
Figure 5B:
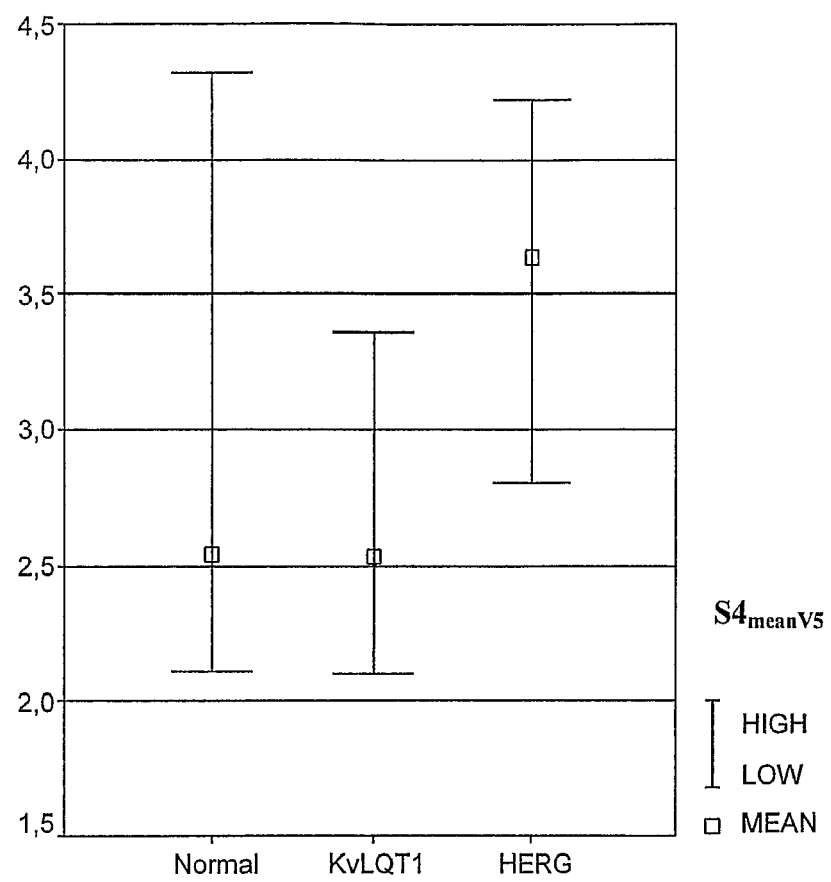
Figure 5C:
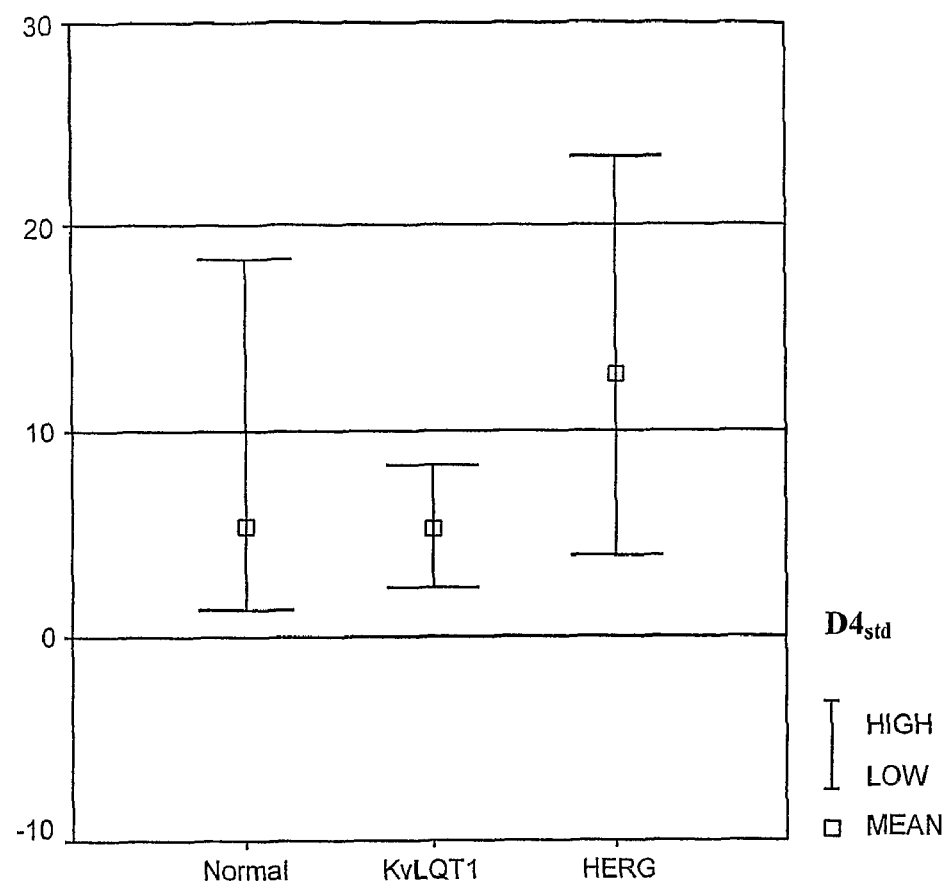
Figure 5D:
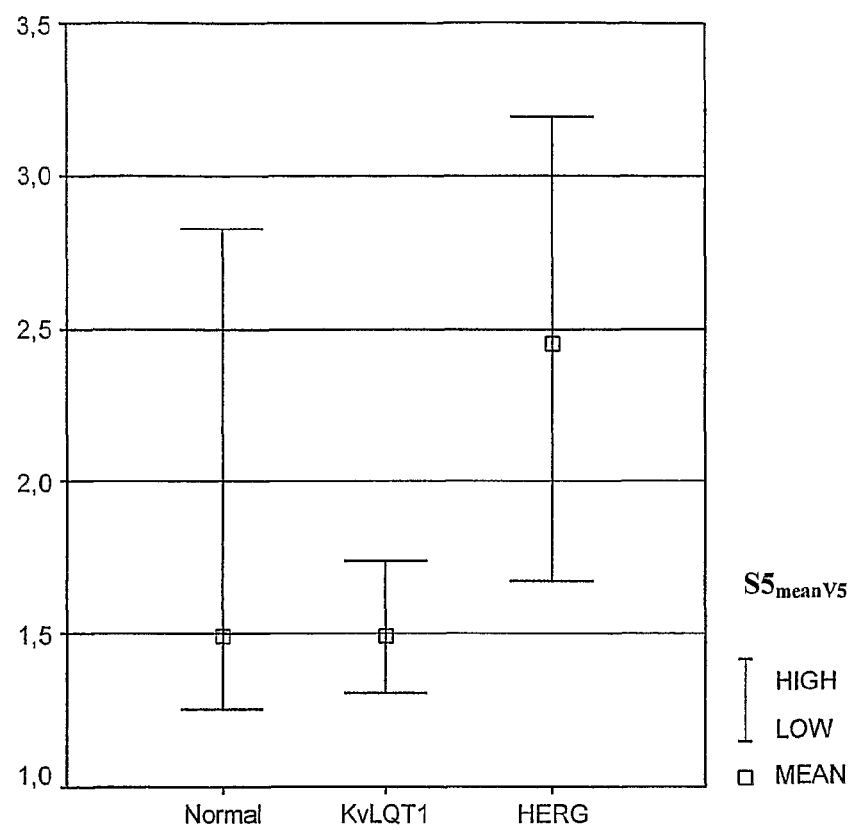
Figure 5E:
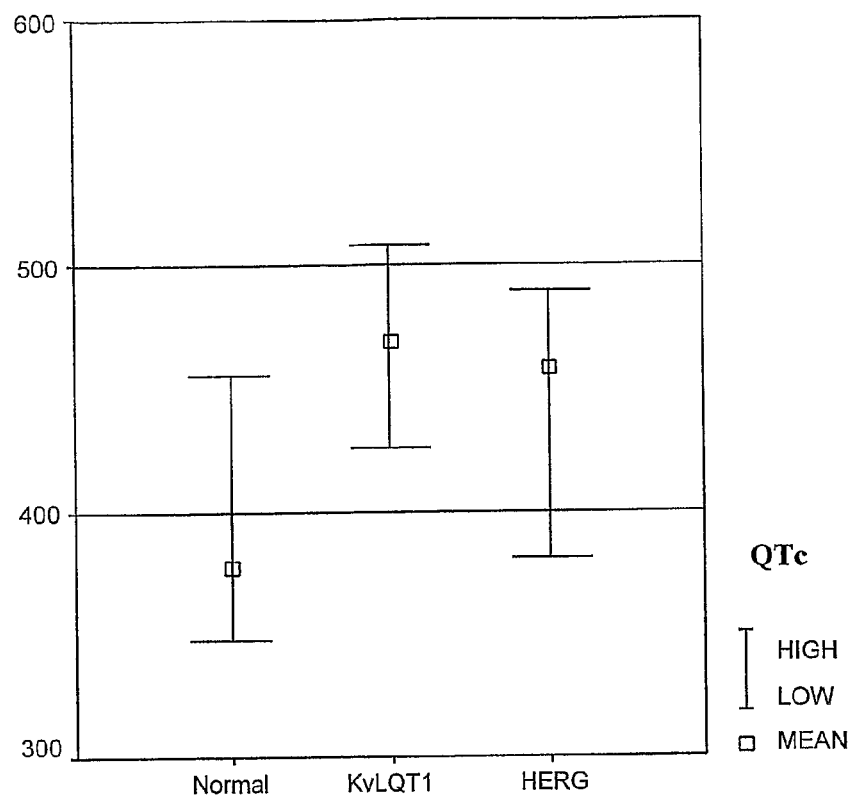

FIG. 4. Scatterplot showing classification of individuals by genotype. Separation of groups was carried out by 2 discriminant functions with 5 variables that characterize repolarisation by computation of symmetry, flatness and duration.

3. RESULTS

The discriminant functions were based on data from all KvLQT1, HERG and normal subjects. The 5 parameters included in both discriminant functions are listed in table 2.

The discriminative efficiency of both generated functions was statistically significant after inclusion of all 5 parameters (function 1: $p<0.0001$, function 2: $p<0.005$).

Variables Entered

| Step | Entered |
| --- | --- |
| 1 | F11std |
| 2 | QTcmeanV5 |
| 3 | S5meanV5 |
| 4 | D4std |
| 5 | S4meanV5 |

Table 2. Variables used by the two discriminating functions. Stepwise introduction of more variables improved the ability of the functions to discriminate between KvLQT1, HERG and normal.

A scatterplot was generated from the discrimination functions and groupings of individual genotypes can be seen in FIG. 4. The dotted lines were read from the SPSS generated territorial map and manually added. The lines reflect borderlines where the differences between each pair of discrimination functions are zero. All 16 processed ECG's were correctly classified and showed at least one discriminatory characteristic as defined by the 5 parameters included in the discrimination functions. Cross validation of both discriminant functions was done with the leave-one-out method and all 16 subjects were again correctly grouped. Reducing the number of variables resulted in misclassified cases due to lack of one or more discriminatory characteristics. In light of this finding we elected to perform further analysis of the selected parameters in order to investigate the individual contributions of each variable to the separation of the three primary groups of subjects. Extreme values for all parameters were identified and the mean was computed.

The result is plotted in FIG. 5. As expected the extent of interlead flatness variation observed in HERG and normal individuals was lower than that found in KvLQT1 subjects. This is evidenced by the F11std parameter in FIG. 5a. When evaluating parameter values S4meanV5 and S5meanV5 (FIG. 5b, d) the extent of asymmetry in KvLQT1 and normal was generally less than that of HERO individuals. Both S4meanV5 and S5meanV5 are symmetry parameters and asymmetry in HERG individuals was augmented in two ways: When bifid T-waves were present the interval from Tstart to Ttop was prolonged due to the definition of Ttop used in this study (the last highest point on the T-wave). Also, when the initial portion before Ttop was pro-longed in HERG individuals better discrimination was possible. Both phenomena were observed in HERG subjects. Generally the Bazett corrected QTc observed in HERG and KvLQT1 was higher than that of normal individuals (FIG. 5e). However overlap existed between all three groups preventing separation of the groups by QTc. Since no single parameter included in the discrimination functions was able to separate KvLQT1, HERG and normal, we proceeded to investigate the classification efficiency provided by the three primary categories represented by the parameters in the functions. This was carried out by generating new discrimination functions using parameters from one category only while excluding the other two. Then, from the new discrimination functions three additional functions were generated, this time allowing the inclusion of parameters from combinations of two categories. Scatterplots illustrating the results of this analysis are shown in FIGS. 6a-f. The first two functions (FIG. 6a) included parameters that characterize the symmetrical properties of the Twave. 83.1% of the 16 subjects were correctly classified. Arrows in FIG. 6a indicate the 3 misclassified subjects. A second discriminant analysis was performed using flatness parameters. This resulted in 93.8% correctly classified subjects. Only one subject was not correctly classified as indicated by the arrow on FIG. 6b. The misclassified case was the same HERG subject incorrectly classified using symmetry parameters. The discriminatory efficiency of duration parameters was also evaluated. Discrimination analysis resulted in 93.8% correctly classified subjects. One HERG subject was mis-waves similar to those found in KvLQT1. However the duration parameters failed to identify this morphological feature, thus reducing classification performance.

It can be noted that improved classification was obtained using flatness or duration parameters versus symmetry parameters and it seemed reasonable to investigate if further classification improvement could be achieved using a combination of several parameter categories.

FIG. 5. a) F11std—Interlead standard deviation of the ratio between the total area under the T-wave from Ttop to Tend and the corresponding time interval. b) S4meanV5—Lead V5 mean modified skewness evaluated in a symmetrical interval surrounding Ttop and corresponding to 20% of the interval between Tstart-Tend. c) D4std—Interlead standard deviation of the time interval from Ttop to Tend. d) S5meanV5—Lead V5 mean of the ratio between the time interval from Tstart to Ttop and the corresponding time interval from Ttop to Tend. e) Lead V5 mean QTc.

Figure 6A:
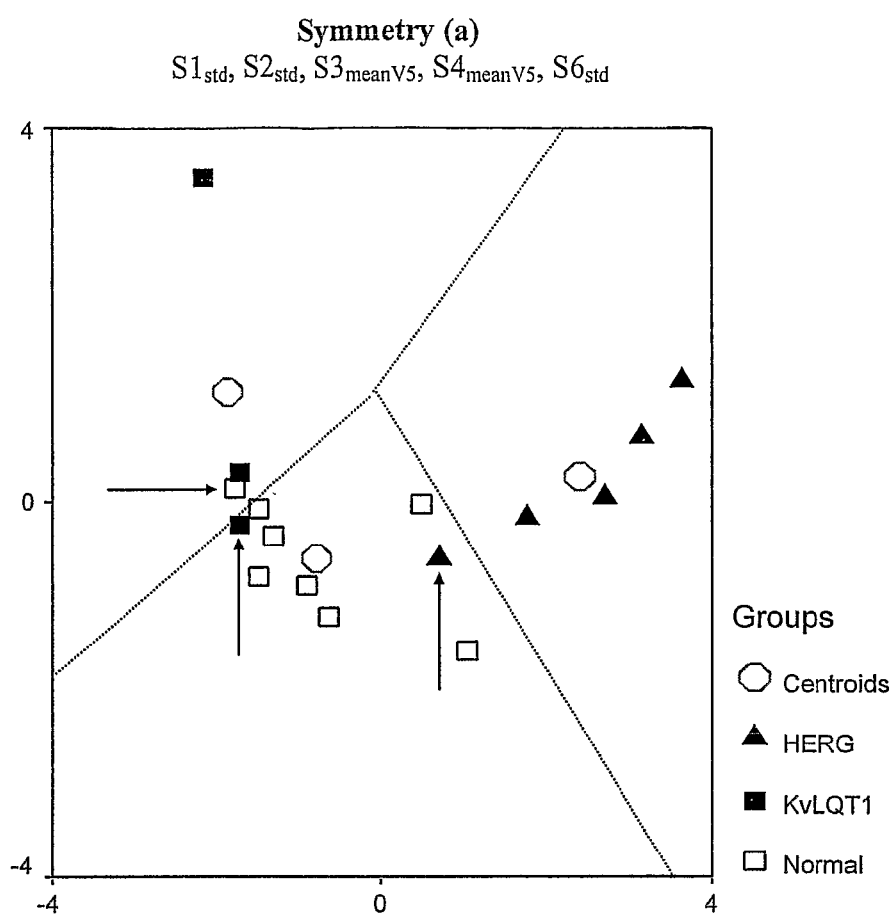
Figure 6B:
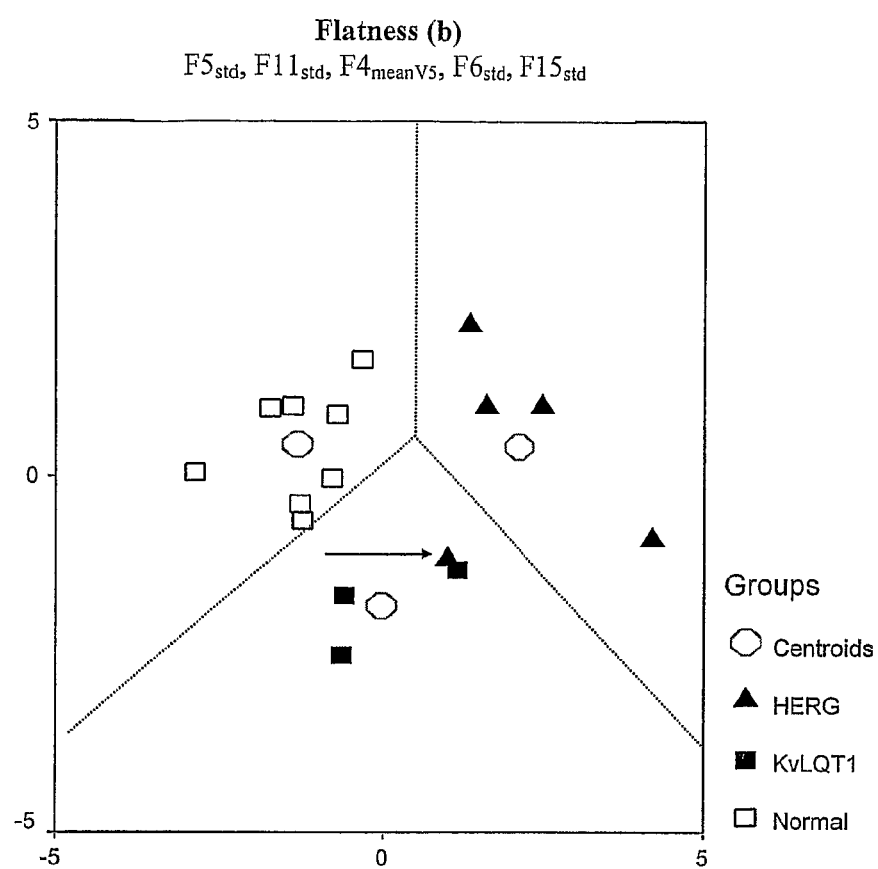
Figure 6C:
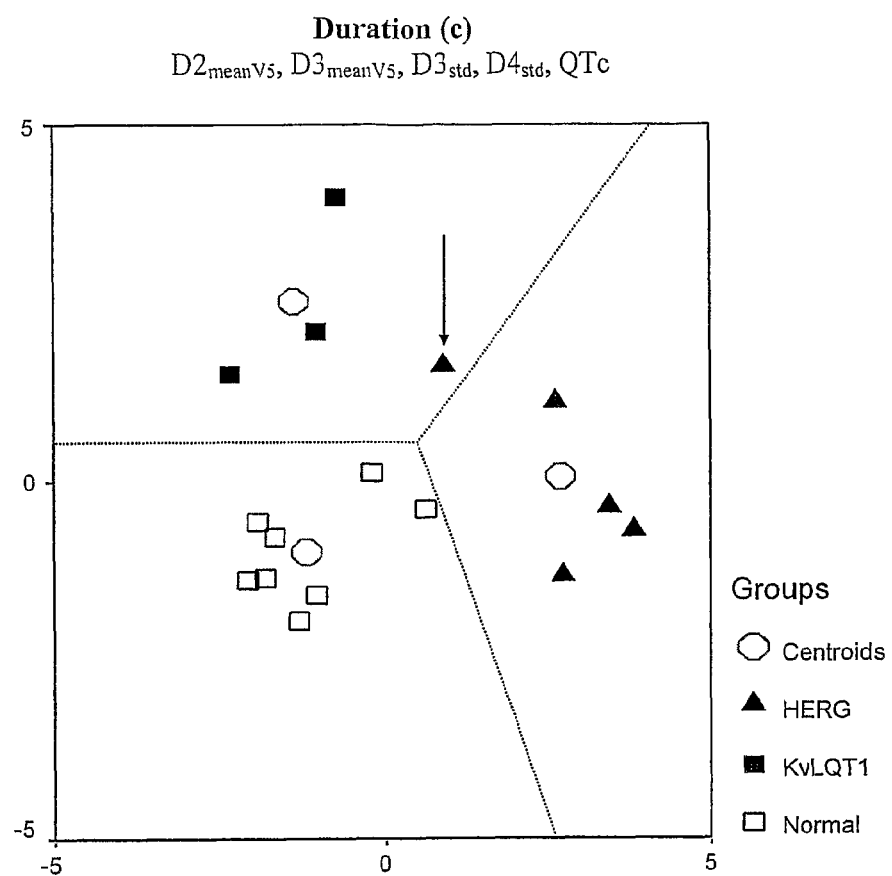
Figure 6D:
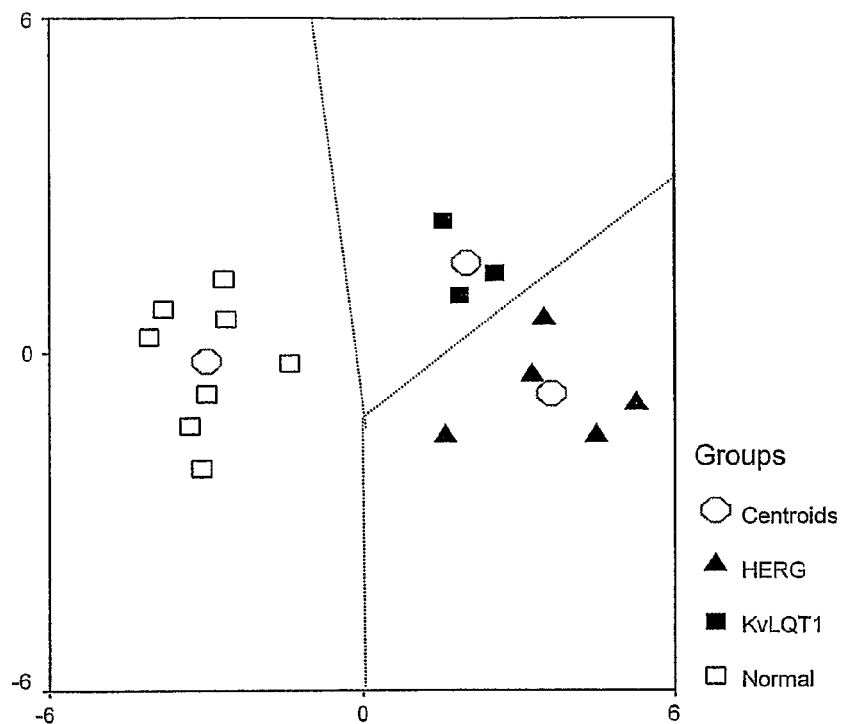
Figure 6E:
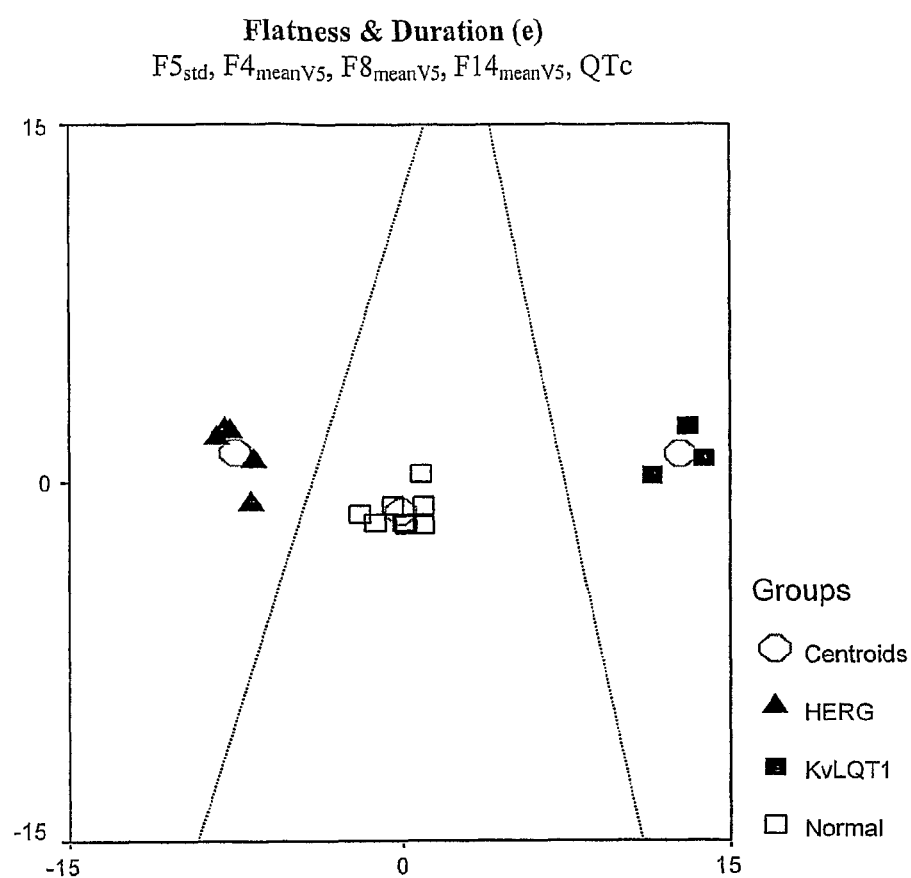
Figure 6F:
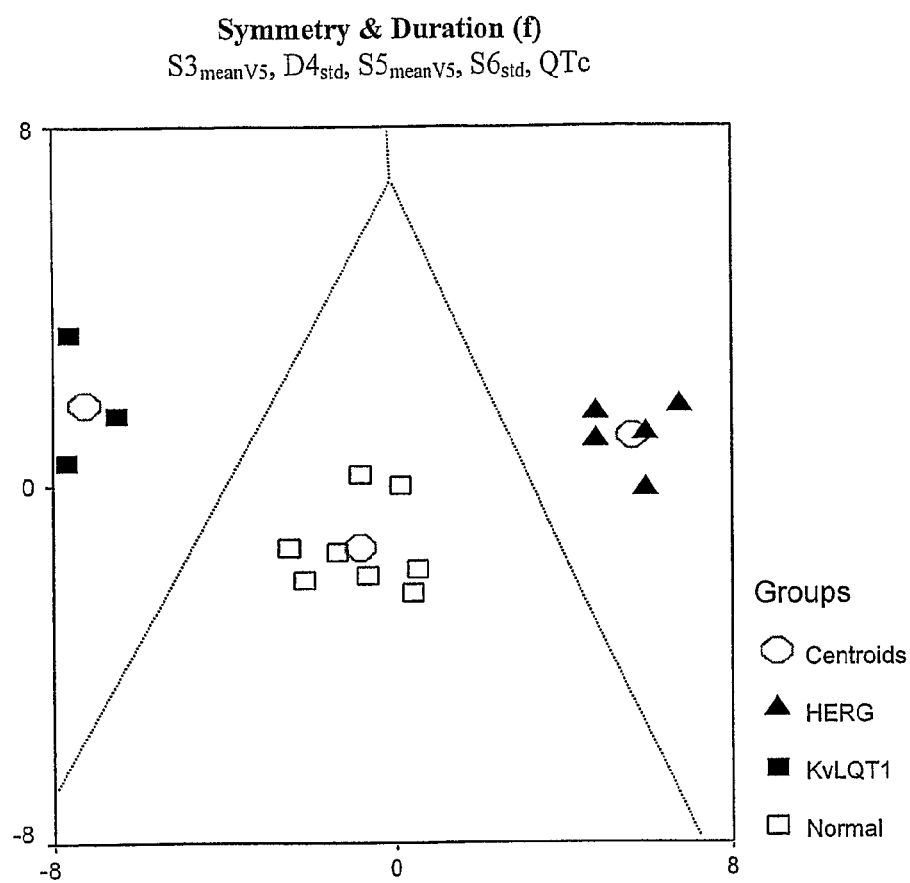

FIGS. 6d-f show the results of three separate discriminant analysis using combinations of parameters from two categories. It can be noted that classification of subjects was perfect in all cases, even when repolarisation duration was not considered (FIG. 6d).

4. CONCLUSION AND DISCUSSION

The initial discriminant analysis performed in this study resulted in perfect classification of all KvLQT1, HERG and normal subjects. In table 2 it was noted that the discriminant functions included parameters from all three categories; T-wave symmetry, T-wave flatness and duration. This is in agreement with the initial hypothesis that a combination of repolarisation duration and T-wave morphology characteristics could improve discrimination between KvLQT1, HERG and normal.

To understand why some subjects were misclassified using a reduced set of parameter categories (FIGS. 6a-c) the duration parameters and morphological characteristics of all 16 ECG's were examined.

Using only symmetry parameters, 3 subjects were misclassified. However no obvious visual characteristics on the three misclassified ECG's could be identified that explained the incorrect classifications. The Bazett corrected QTc was 347 ms for the normal subject, 425 ms KvLQT1, 476 ms HERG. Although an obviously prolonged QTc was present in the misclassified HERG subject it was not identified using symmetry parameters alone.

Discriminant analysis using parameters from the flatness category resulted in only 1 misclassification. Again no visual characteristics were identified to account for the misclassification. Although it was anticipated that the FIG. 6. a) The result of discriminant analysis using symmetry parameters resulted in three misclassified cases (arrows). Visual inspection of the ECG's revealed no apparent abnormalities to indicate the reason for incorrect misclassification. b) The result of discriminant analysis using flatness parameters. One incorrectly classified HERG subject was identified (arrow) even though no obvious visual abnormality indicated a different genotype. c) Result of discriminant analysis using duration parameters. This result illustrates the failure of duration parameters to discriminate between KvLQT1, HERG and normal (arrow). d-e) Combinations of parameters from two categories illustrate the improvement in classification efficiency when compared to FIGS. 6a-c evaluation of T-wave flatness would be able to discriminate HERG from KvLQT1 subjects this was not accomplished by using flatness as a single descriptor of repolarisation. Performing discriminant analysis based on the QTc parameter as the only variable resulted in 1 misclassification. This was not unexpected since it is well known that a substantial overlap in QTc values can exist between normal and affected individuals. The lack of unambiguous discrimination between all groups by use of the QTc parameter alone emphasizes the hypothesis that additional parameters are needed to classify LQTS individuals. By combining parameters from two categories it was found that the discriminatory strength was increased.

(FIGS. 6d-f) This was evidenced by the fact that no subjects were misclassified using two categories. A particularly interesting finding, was the perfect separation of all subjects that was obtained using symmetry and flatness parameters with no duration parameters included. This result implies the discriminatory strength inherent in parameters from those two categories. In addition it was found that symmetry or flatness parameters combined with duration parameters yielded perfect discrimination between all groups. Results from the discriminant analysis using one and two categories indicate that a combination of more parameter categories strengthen the overall discriminatory power of the classification functions. Combining these findings with the results from the three category discriminant analysis initially performed, it is reasonable to speculate that a substantially improved discrimination between KvLQT1, HERG and normal is possible using all three categories of parameters.

In light of the results obtained in this study we propose a new technique for discriminating between KvLQT1, HERG and normal subjects. Through multivariate discriminant analysis it was found that a combination of two duration parameters and three T-wave symmetry- and flatness parameters was sufficient to classify each of the 16 study subjects into one of the three distinct groups. Although no single parameter had the necessary discriminatory strength to classify the subjects, the combination of multiple parameters in two discrimination functions was statistically significant (function 1: $p<0.0001$, function 2: $p<0.005$). The encouraging results of multivariate repolarisation analysis found in this study support the use of symmetry-, flatness- and duration parameters to classify LQTS patients.

The use of the proposed multiple parameter categories to classify KvLQT1 and HERG genotypes may prove to be a powerful clinical tool in the making.

The invention claimed is:

1. A system for analyzing ECG curvature, the system comprising:
    input means; and
    an ECG source,
    wherein the system is configured to isolate and store at least one among a number of different parameters,
    wherein the input means is connected to the ECG source,
    wherein the system is configured to indicate and/or isolate different parameters of a received ECG curvature to indicate symptoms,
    wherein the system is configured to combine, in at least a first mathematical analysis, a plurality of selected parameters from a number of groups of parameters including symmetry, flatness, duration and/or complexity,
    wherein the system is configured to represent a result of the analysis as a point in at least one coordinate system having at least one axis,
    wherein the system is configured to compare actual coordinates in the coordinate system with a number of reference parameters stored in the system, to indicate symptoms or diseases having influence on the ECG curvature,
    wherein the system is configured to analyze a QT curvature of the ECG to indicate hereditary or acquired Long QT Syndrome.

2. A system for analyzing ECG curvature according to claim 1 wherein the system is configured to analyze the ECG curvature for Long QT Syndrome acquired by drug influence.

3. System according to claim 1, wherein the system is configured to repeat the analysis of the QT curvature for further selected parameters in order to achieve more reliable results.

4. System according to claim 1, wherein said plurality of selected parameters is selected at least from the symmetry group of parameters, and wherein the symmetry group of parameters comprises at least one of the following parameters:
    S1 Symmetry evaluated from Tstart to Tend;
    S2 Symmetry with Tpeak as mean evaluated from Tstart to Ten;
    S3 Symmetry with Tpeak as mean evaluated in a symmetric interval of 10% of the Tstart-Tend-interval surrounding Tpeak;
    S4 Symmetry with Tpeak as mean evaluated in a symmetric interval of 20% of the Tstart-Tend-interval surrounding Tpeak;
    S5 Ratio of the time interval "Tstart to Tpeak" and the time interval "Tpeak to Tend;
    S6 Ratio of the average slope from Tstart to Tpeak and from Tpeak to Tend;
    S7 Variation evaluated from Tstart to Tend, calculated by the formula;
    S8 Variation with Tpeak as mean evaluated from Tstart to Tend;
    S9 Variation with Tpeak as mean evaluated in a symmetric interval of 10% of the Tstart-Tend-interval surrounding Tpeak;
    S10 Variation with Tpeak as mean evaluated in a symmetric interval of 20% of the Tstart-Tend-interval surrounding Tpeak;
    S11 The Hill parameter, $K_m$, evaluated by least square fitting of the repolarization integral, RI(t), from the Jpoint to the following Ponset; and
    S12 The Hill parameter, $K_m$, evaluated by least square fitting of the repolarization integral, RI(t), from Tstart to Tend.

5. System according to claim 1, wherein said plurality of selected parameters is selected at least from the flatness group of parameters, and wherein the flatness group of parameters comprises at least one of the following parameters:
    F1 Flatness evaluated from Tstart to Tend;
    F2 Flatness parameter, F1, normalized by the size of the R wave;
    F3 Flatness with Tpeak as mean evaluated from Tstart to Tend;
    F4 Flatness parameter, F3, normalized by the size of the R wave;
    F5 Flatness with Tpeak as mean evaluated in a symmetric interval of 10% of the Tstart-Tend-interval surrounding Tpeak;
    F6 Flatness parameter, F5, normalized by the size of the R wave;
    F7 Flatness with Tpeak as mean evaluated in a symmetric interval of 20% of the Tstart-Tend-interval surrounding Tpeak;
    F8 Flatness parameter, F7, normalized by the size of the R wave;
    F9 Ratio of the total area under the T-wave from Tstart to Tpeak and the corresponding time interval;
    F10 Flatness parameter, F9, normalized by the size of the R wave;
    F11 Ratio of the total area under the T-wave from Tpeak to Tend and the corresponding time interval;
    F12 Flatness parameter, F11, normalized by the size of the R wave;
    F13 Ratio of the total area under the T-wave, from Tstart to Tend and the corresponding time interval;
    F14 Flatness parameter, F13, normalized by the size of the R wave;
    F15 Ratio of the T wave height and the T wave width;
    F16 The T wave height;
    F17 Average slope from Tstart to Tpeak;
    F18 Average slope from Tpeak to Tend;
    F19 The Hill parameter, n, evaluated by least square fitting of the repolarization integral, RI(t), from the Jpoint to the following Ponset;
    F20 The Hill parameter, n, evaluated by least square fitting of the repolarization integral, RI(t), from Tstart to Tend;
    F21 The Hill parameter, $V_{max}$, evaluated by least square fitting of the repolarization integral, RI(t), from the Jpoint to the following Ponset; and
    F22 The Hill parameter, $V_{max}$, evaluated by least square fitting of the repolarization integral, RI(t), from Tstart to Tend.

6. System according to claim 1, wherein said plurality of selected parameters is selected at least from the duration group of parameters, and wherein the duration group of parameters and comprises at least one of the following parameters:
    QTc The Q-T interval normalized by the square root of the R-R interval according to Bazett's formula;
    D2 The time interval from Tstart to Tend;
    D3 The time interval from Tstart to Tpeak; and
    D4 The time interval from Tpeak to Tend.

7. System according to claim 1, wherein said plurality of selected parameters is selected at least from the complexity group of parameters, and wherein the complexity group of parameters comprises at least one of the following parameters:

C1: Number of local maxima between Tstart and Tend; the minimum number is one; and C2: Number of phases between Tstart and Tend, where a phase is defined as a singly connected part of the wave that is entirely above or entirely below the iso-electric line; the minimum number is one.

8. System according to claim 1, wherein the system is configured to select and combine parameters from the different groups.

9. System according to claim 1, wherein the system is configured to be trained during use, wherein the parameters' values are calculated for individual subjects, wherein the mathematical analysis of the parameters determines at least one optimal small parameter set out of the complete number of parameters from all categories.

10. System according to claim 1, wherein the final classification function is at least based on data from at least one LQT or drug influenced group and Normal subjects stored as a training set, with the consequences that the classification is improved by adding new subjects to the training set, wherein the new subject are tailored to demographic or gender differences.

11. Method for analyzing drug influence on ECG curvature having a number of parameters, the method comprising:
receiving ECG curvature from a source,
indicating a number of different parameters contained in the received ECG curvature,
storing the parameters in storage means,
selecting disease specific parameters in the storage means,
selecting parameters from groups of parameters including symmetry, flatness, duration and/or complexity,
combining selected parameters in mathematical analyzing means,
representing the result of the mathematical analysis as a point in at least one coordinate system having at least one axis,
comparing the actual placement in the coordinate system with a number of reference parameters stored in a memory, and
analyzing the QT curvature of the ECG for indicating drug induced changes.

12. Method according to claim 11, the method further comprising repeating the analyzing process for further selected parameters for achieving more reliable results.

13. Use of a system for analyzing ECG curvature for test of drugs,
wherein the system has input means connected to an ECG source, comprising the steps of:
isolating and storing at least one among a number of different parameters in the system,
indicating and/or isolating the different parameters of a received ECG curvature for indicating possible symptoms,
combining a number of selected parameters in at least a first mathematical analysis, and representing the result of the analysis as a point in at least one coordinate system, comprising at least one axis,
using the system to compare the actual placement in the coordinate system with a number of reference parameters stored in the system, for indicating symptoms having influence on the ECG curvature,
calculating the parameters of the ECG curvature before and after a drug test for a number of subjects,
calculating the difference for selected parameters between before and after testing for each subject,
using the system to analyze the QT curvature of the ECG for indicating acquired Long QT syndrome, and
providing a statistical analysis of selected parameters for a number of subjects that gives statistical significance for at least one of the following decisions:
"acceptance of the drug",
"rejection of the drug", and
"further testing of the drug".

14. Use according to claim 13, wherein the input means connected to an ECG source is at a first location and the decisions are transmitted to a second location.

15. Use according to claim 14, wherein the first location is in an ambulance on its way to a hospital and the second location is the hospital.

16. System according to claim 1, wherein the input means and ECG source are at a first location and wherein the system is adapted to transmit an analysis output to a second location.

17. Method according to claim 16, wherein the first location is in an ambulance and the second location is a hospital.

* * * * *